(12) United States Patent
Melles

(10) Patent No.: US 8,523,644 B2
(45) Date of Patent: Sep. 3, 2013

(54) OPERATION UNIT

(75) Inventor: Gerrit Reinold J. Melles, Rotterdam (NL)

(73) Assignee: Medical Technology Transfer Holding B.V. (NL)

( * ) Notice: Subject to any disclaimer, the term of this patent is extended or adjusted under 35 U.S.C. 154(b) by 1231 days.

(21) Appl. No.: 10/808,718

(22) Filed: Mar. 25, 2004

(65) Prior Publication Data
US 2006/0149120 A1 Jul. 6, 2006

(30) Foreign Application Priority Data

Mar. 28, 2003 (EP) .................................... 03075907

(51) Int. Cl.
B01L 1/04 (2006.01)
(52) U.S. Cl.
USPC ........................................................ 454/187
(58) Field of Classification Search
USPC .................. 454/187, 188, 190, 191, 192, 197
See application file for complete search history.

(56) References Cited

U.S. PATENT DOCUMENTS

| 3,151,929 | A | | 10/1964 | Potapenko | 21/74 |
| 3,602,212 | A | | 8/1971 | Howorth | 128/1 R |
| 3,893,457 | A | * | 7/1975 | van der Waaij | 128/847 |
| 3,954,429 | A | * | 5/1976 | van der Waaij | 96/136 |
| 4,038,974 | A | * | 8/1977 | Pielkenrood | 128/847 |
| 4,742,764 | A | * | 5/1988 | Duvlis | 454/190 |
| 4,936,318 | A | * | 6/1990 | Schoolman | 128/847 |
| 5,314,377 | A | * | 5/1994 | Pelosi, III | 454/187 |
| 6,966,937 | B2 | * | 11/2005 | Yachi et al. | 55/385.2 |

FOREIGN PATENT DOCUMENTS
WO        WO 95/16168        6/1995

* cited by examiner

Primary Examiner — Steven B McAllister
Assistant Examiner — Samantha Miller
(74) Attorney, Agent, or Firm — Banner & Witcoff, Ltd.

(57) ABSTRACT

An operation unit, comprising a wall and an air flow unit, said air flow unit being provided with means for filtering said air, said wall being provided with at least one opening and a cover, covering at least part of said opening, said air flow unit comprising at least one air outlet opening for directing air from said air flow unit over said cover, air inlet means preferably being provided for retracting air to said air flow unit.

17 Claims, 7 Drawing Sheets

OPERATION UNIT

Figure 1:
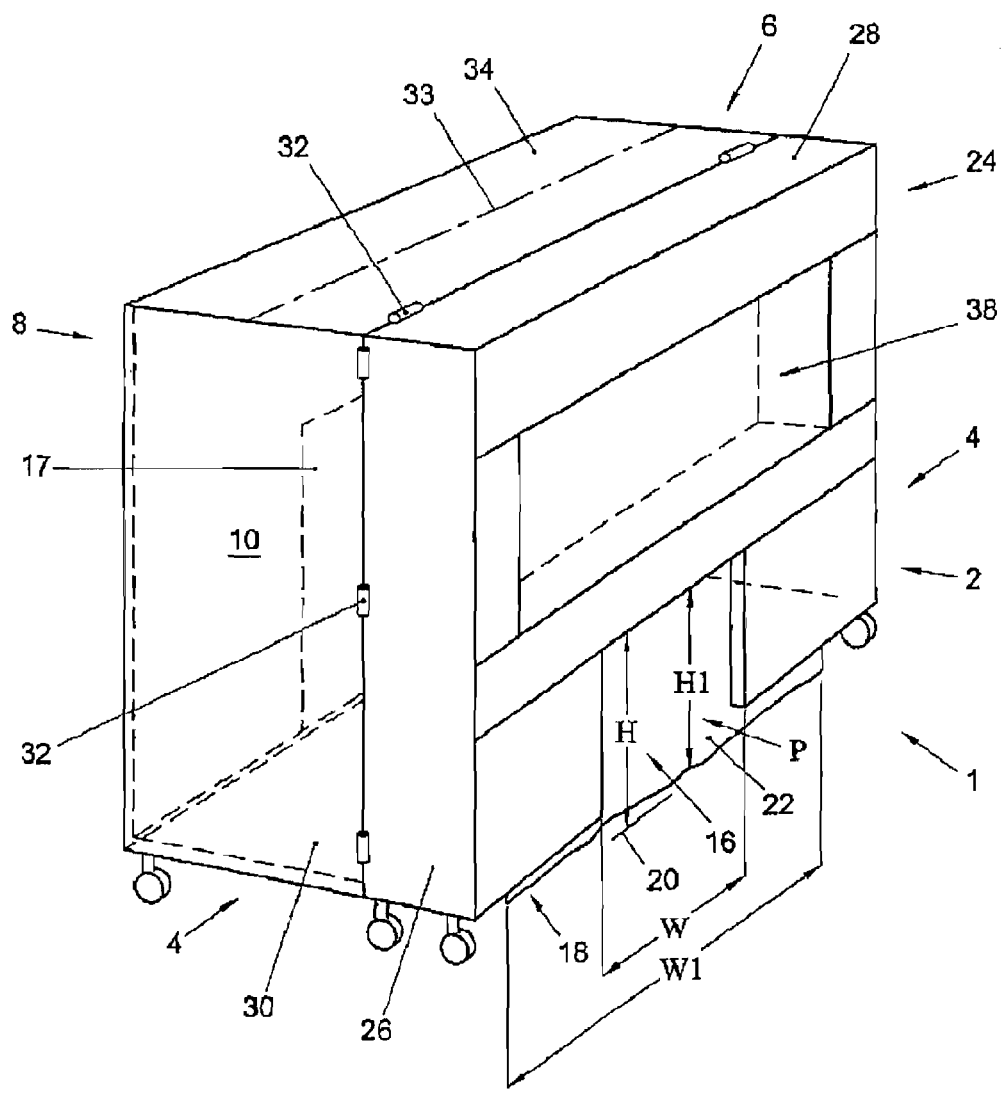

This application claims the benefit of the filing date of European application no. EP 03075907.0, filed Mar. 28, 2003, which is hereby incorporated herein by reference.

The invention relates to an operation unit.

Ordinarily, surgery on human beings or animals is performed in operation theatres, rooms which are especially adapted for surgery under sterile circumstances. Such operation rooms are space consuming and very costly, due to for example the expensive installation for cleaning the air, maintaining a slight overpressure within said room and for sterilisation of all operating tools and the like. Moreover, since such operation room has to be suitable for all kinds of surgery, more equipment will be present in said room than necessary for each individual type of surgery.

A further disadvantage of such operation rooms is that everybody who has to attend said surgery, such as the or each surgeon, nurse, anaesthetist, technician or other persons necessary for performing the surgery has to be especially clothed and perform specific cleaning before entering said room, as should the complete patient. This is also time consuming, expensive and, if not performed well, may lead to contamination of the operating area, which will be detrimental to the patient. A still further problem of such operation room is that people leaving and/or entering said room will lead to air turbulences, which may also be detrimental to the sterility of the room in general and specifically to the patient.

A still further disadvantage is that the know operating rooms have to be build in and are static. Patients have to be brought to said room for surgery.

The present invention relates to operation units. An object of the present invention is to provide an operation unit which is easy in use.

Furthermore the present invention aims to provide an operation unit which is relatively small and less expensive then a known operation room.

A further object of the present invention is to provide an operation room which allows operation assistants, anaesthetists, nurses, technicians and the like freedom of movement during preparation for and performing surgery.

A still further object of the present invention is to provide for an operation unit which minimises the need for sterilisation.

At least a number of these and further objects and advantages are provided for by an operation unit as characterised by the features of claim 1.

An operation unit according to the present invention is arranged such that only the relevant part of a patient and a surgeon performing surgery have to be within a space comprising means for providing a sufficiently sterile surrounding for said surgery. A relevant part of the patient has to be understood as the part of the patients body on or in which surgery has to be performed. For example, for eye surgery only the patients head has to be introduced into said space, under a cover leaving available to the surgeon only the eye of the patient and possibly the direct surrounding thereof. The desired sterile surrounding is provided for by an air flow over said cover and said relevant part of said patient.

Due to these characteristics an operation unit according to the present invention can be build relatively small and economically. Furthermore, the people and apparatus or other equipment which is not to be used in said sterile surroundings, such anaesthetics, monitoring equipment and the like can be kept outside said unit. Moreover, said people can come and go from near said patient without the necessity of special clothing, cleaning or the like. Also air turbulences around said unit are to a high degree not detrimental to said patient. Moreover said unit allows surgery on parts of said body without the necessity of special cleaning and/or clothing of the patient. A still further advantage of said unit is that it can be build light and easily displaceable. If build mobile it can be set up virtually anywhere where surgery has to be performed.

A unit according to the present invention is apart from said wall, which will further on also be referred to as front wall, preferably provided with side walls, a roof and a back wall, such that a space is enclosed, shielded from the surrounding. The unit is preferably at least partly foldable, such that it can be brought in an ever smaller storage position.

The side walls and roof element are preferably foldable over and/or against said flow unit, wherein the back wall may be made foldable and/or made of strip-like elements, such that said space can easily be entered or left through said back wall.

In an operation unit according to the present invention, said cover element is preferably made of a flexible, pliable and/or drapeable material, such as cloth. For example a surgery blanket. During use such cover can easily be folded or plied over part of a body to be operated on, such as a head, abdomen, foot or the like. One or more openings can easily be provided in said cover for revealing an operation site such as an eye, abdomen, foot or the like. The top of said cover is preferably positioned against the front wall, such that air from said flow unit will substantially be directed over said cover in said space.

The at least one opening in said at least one wall is preferably dimensioned such that at least an end of a hospital bed, stretcher or the like can be inserted through said opening under said cover. The opening can for example be between 20 and 90 cm wide and between 20 and 120 cm high. These dimensions are only given as examples and should by no means be considered as limiting the scope of protection sought.

In an alternative embodiment the opening is made such that an extremity of a human or animal can be inserted through said opening, such that for example a hand, foot, hoof or the like can be entered into said space under said cover, leaving the rest of the body outside said space. An opening in said wall could also be provided with means for adjustment of the width and/or the height, such that at all times the most appropriate size of said opening can be obtained.

In an advantages embodiment the outlet opening connected to the flow unit is dimensioned such that it extends over at least the width of said at least one opening in said wall, such that across said opening an air flow can be obtained during use. This provides for a very advantageous screen against contamination.

The direction of the outflow opening is preferably such that air streaming from said outflow opening is directed downward, more preferably downward in a direction away from said wall, in which said opening is provided. This means that an airflow is provided over said cover, into, during use, the direction of a person performing said surgery, away form said wall.

By positioning the at least one air inlet opening lower than said outflow opening said airflow over said cover is even further enhanced.

It is preferred that near the ground on which said operation unit is positioned, openings are provided for connection of an inner space of said unit and the surrounding of said unit, such that turbulence of air within said unit is prevented.

The walls of said operation unit are preferably at least partly made transparent, especially part of the front wall and/or parts of the side walls, such that a person performing surgery within said operation unit has the possibility of visual contact with persons surrounding said operation unit and/or with parts of the patient extending outside said operation unit.

The present invention further relates to a method for preparing a person for surgery, according to claim 15.

In such method, a person can be prepared for surgery very easily, without the necessity of for example full cleaning of the person, changing clothes or preparing a full operation room. Although it is preferred that such method is performed in a substantially clean environment, such is not essential. Since within the operation unit a flow of substantially sterile air is guided over a cover covering the person to be operated, leaving free only at least one operating area of such person, the operation site is kept sterile to the desired degree.

Air may be recirculated within said unit, for various reasons using a flow unit for filtering said air for sterilisation purposes. Sterile has to be understood as at least encompassing air sufficiently clean for operating environment purposes.

The present invention further relates to a method for performing surgery on a person, in which said person is positioned on a bed, stretcher, chair or the like supporting structure, whereby part of the body of said person on which surgery is to be performed is moved through an opening under a cover, especially a cloth, an opening being provided in said cloth disclosing an operation area, a flow of substantially sterile air being guided over said cover and at least said operating area.

Such method has the advantage that surgery can be performed without very extensive cleaning operations of both the patient and all people assisting during said operations. Said people assisting with said operation as well as for example family or other relatives can even enter or leave the room in which said unit is located during said surgery, such that the person on which surgery is to be performed can be comforted, whereas for example anaesthetists and nurses can attend various operations at any one time.

Further advantageous embodiments of an operation unit and methods according to the present invention are given in the dependent claims.

Figure 3:
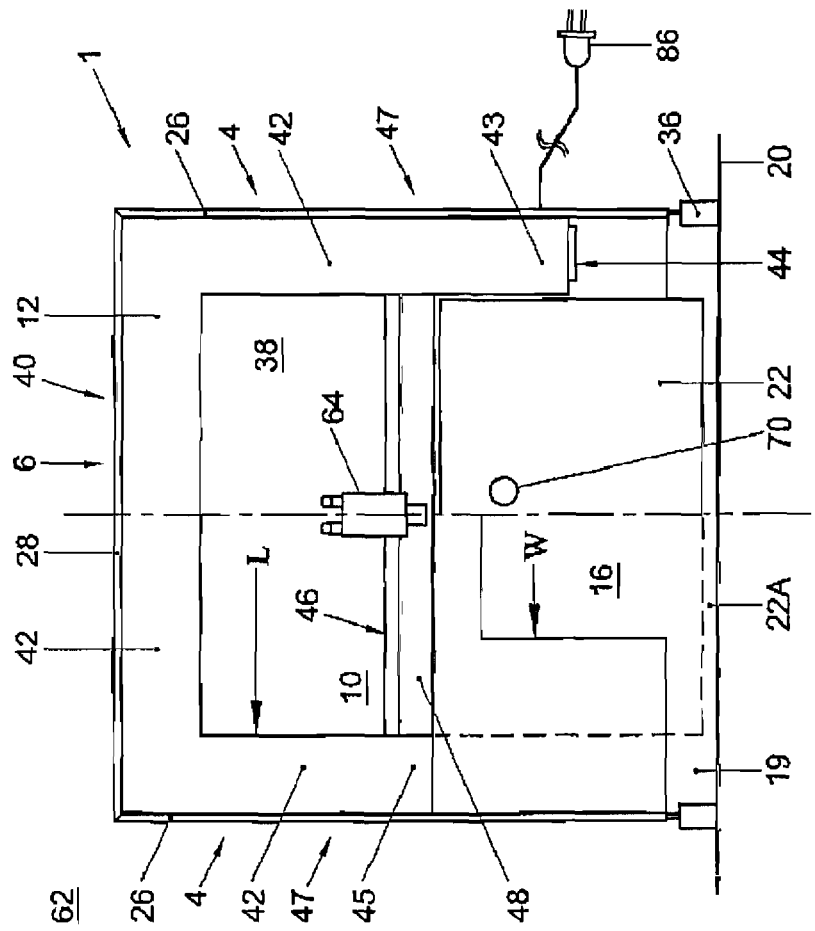
Figure 2:
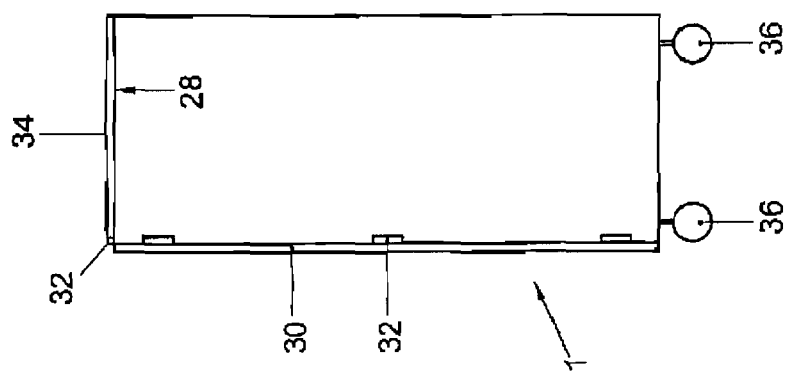
Figure 4:
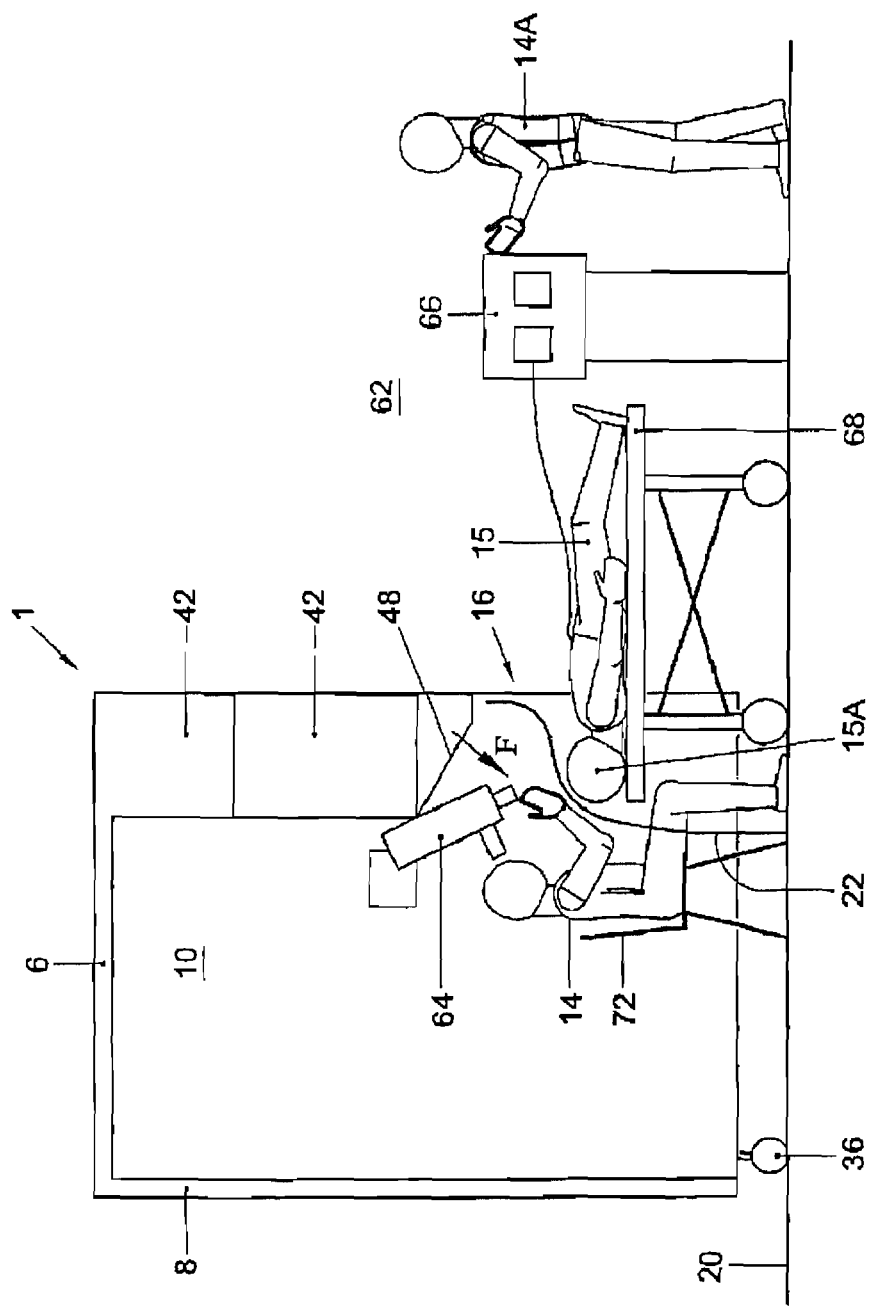
Figure 5A:
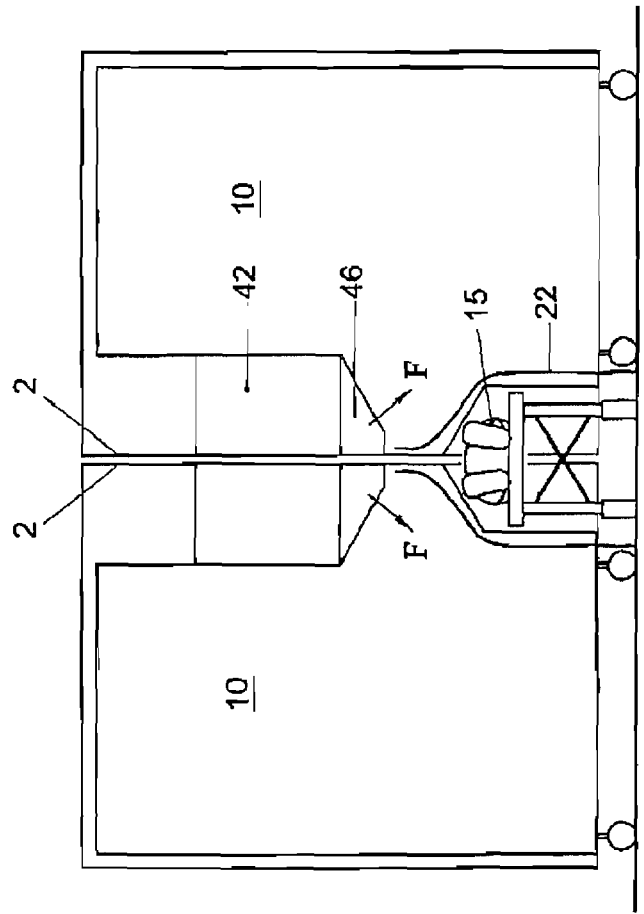
Figure 5:
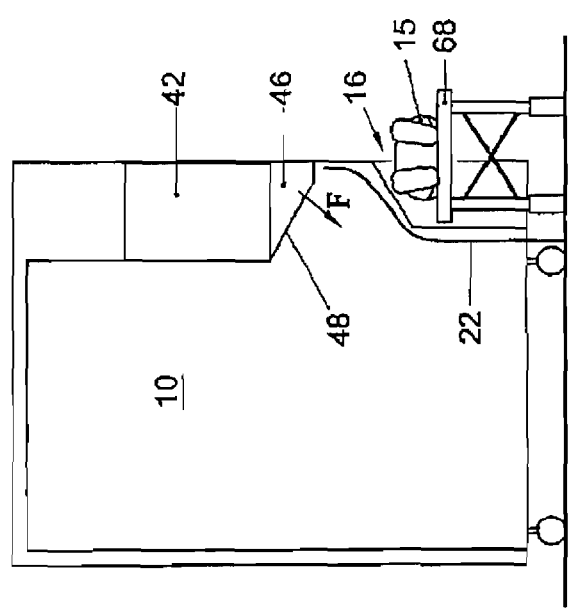
Figure 6:
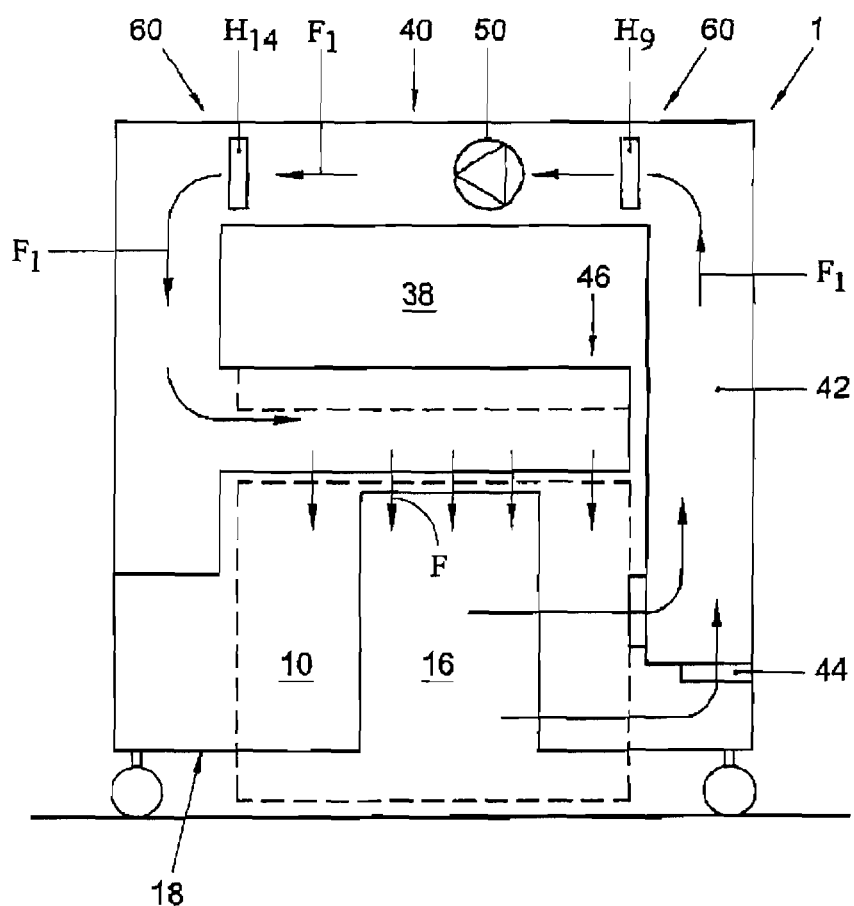
Figure 7:
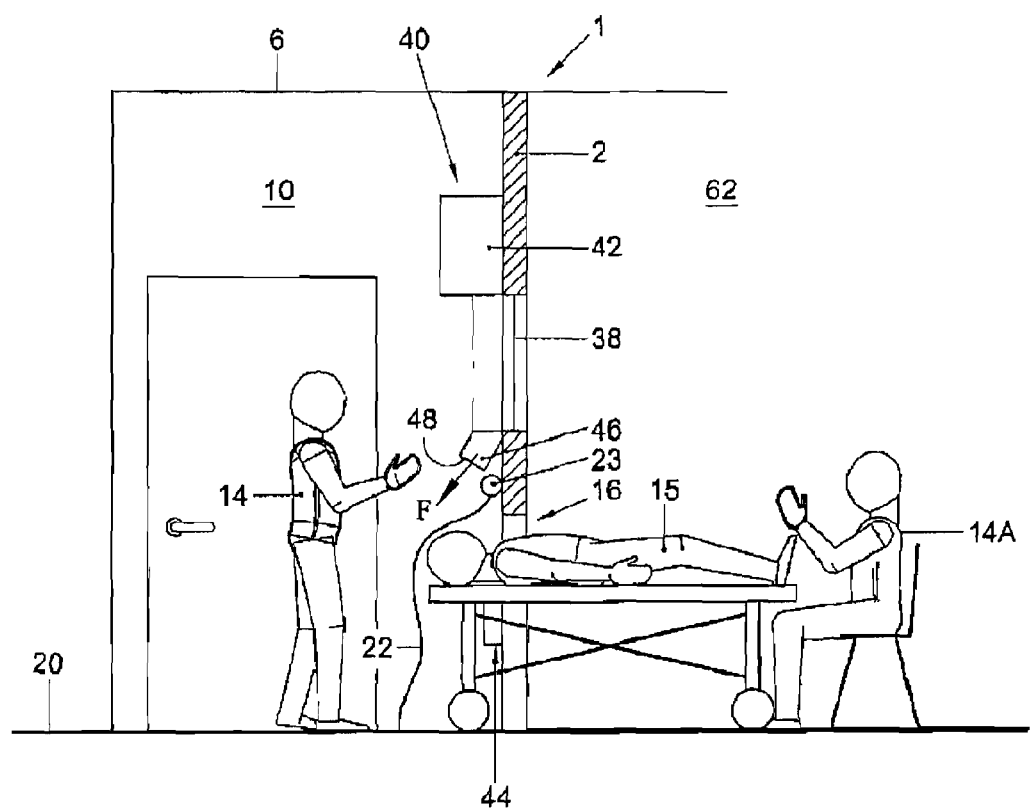
Figure 8:
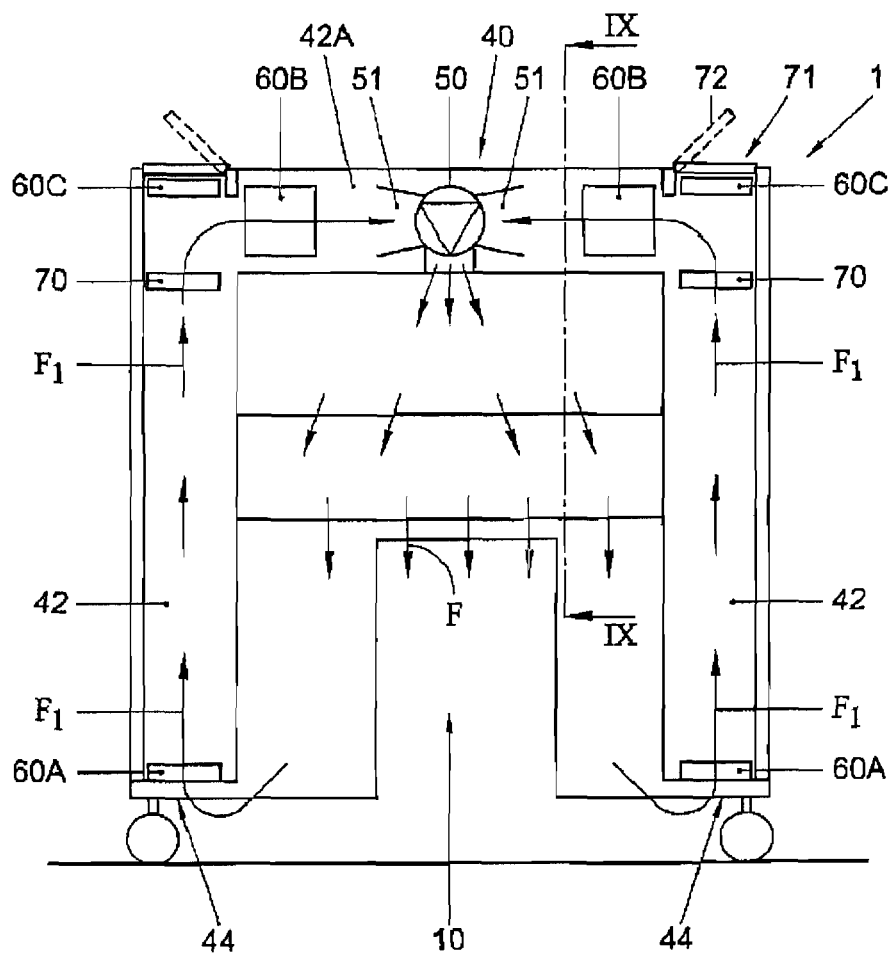
Figure 9:
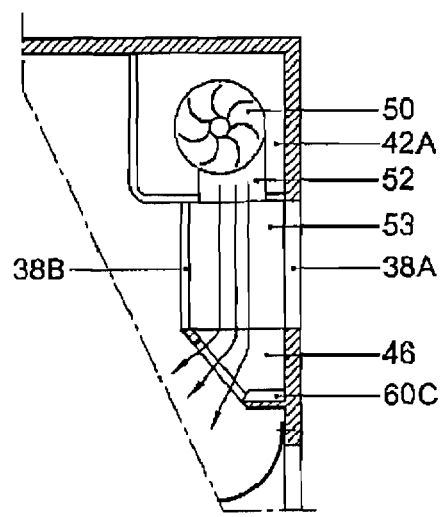

For a better understanding of the present invention embodiments of an operation unit and methods according to the present invention will be elucidated hereafter, referring to the drawings. These show:

FIG. 1 in perspective view schematically an operation unit according to the present invention, in a first embodiment, ready to use;

FIG. 2 in side view schematically an operation unit according to FIG. 1 in a folded position;

FIG. 3 an operation unit according to FIG. 1, in rear view, with broken away a back wall and part of the cover;

FIG. 4 in cross sectional side view an operation unit according to the present invention during surgery;

FIG. 5 an operation unit according to the present invention, in an alternative embodiment, seen in cross-section in side view, ready for operation;

FIG. 5A an operation unit according to the invention, comparable to the unit according to FIG. 5, with two spaces;

FIG. 6 schematically an operation unit according to the present invention, in which is shown the air flow during use;

FIG. 7 in cross-section schematically a further alternative embodiment of an operation unit according to the present invention, during surgery;

FIG. 8 in a view corresponding to FIG. 6, an alternative embodiment of an operation unit according to the present invention, including air flow; and FIG. 9 schematically in cross-section along the line IX-IX in FIG. 8, the operation unit as shown in FIG. 8.

In this description similar elements have similar reference signs. Embodiments of operation units are shown by way of example only. It should be clear that variations thereof are possible, especially combinations of different features of the embodiments shown.

In FIG. 1 an operation unit 1 is shown comprising a front wall 2, two opposite sidewalls 4, connected to said front wall 2 and a top wall or roof 6 connected to said front wall 2 and the sidewalls 4. A back wall 8 is provided, connected to said sidewalls 4 and said roof 6. The front wall 2, sidewalls 4, roof 6 and back wall 8 enclose an inner space 10 within said operation unit 1, sufficiently large for housing at least some operation equipment, a flow unit 12 to be discussed hereafter and at least one person 14 performing surgery, such as an eye surgeon, orthopaedic surgeon or another type of medical specialist. An operation unit 1 according to the present invention can for example be between 2 and 2.5 m high, between 2 and 3 m wide and between 1.5 and 2.5 m deep. These sizes are only given by way of example and are by no means limiting the scope of the present invention.

In the embodiment of the operation unit 1 according to FIG. 1, the front wall comprises an opening 16 extending from a lower side 18 of said front wall 2. For example a hospital bed, stretcher or the like can be driven with a head or foot part thereof into said opening 16 in the direction P. The opening 16 has a height H of for example between 60 cm and 100-120 cm, measured from the ground 20, and has a width W of for example between 60 cm and 1 m. These sizes are also only given by way of example and should by no means be considered as limiting the invention. A cover 22 is suspended from a hanging means 23 such as a series of hooks, a clamping rail, rings or the like, hanging down from above said opening 16 and extending across said opening 16 to close to the ground 20 or even on the ground 20. The width $W_1$ of the cover 22 is larger than the width W of the opening 16, whereas the height $H_1$ of said cover 22 is preferably larger than the height H of the opening 16. When the operation unit 1 is not in use, or at least when a patient is not introduced through said opening 16, as will be explained hereafter, the cover 22 hangs down behind said opening 16, in said inner space 10, closing said opening 16 substantially.

The cover 22 is preferably made of cloth or plastic, such as a surgery blanket and is sufficiently pliable, foldable or the like to be used for covering at least part of a patient to be operated on, as will be discussed hereafter.

The operation unit 1 according to FIG. 1 comprises a front part 24 which is substantially rigid and comprises said front wall 2, two side panels 26 and a top panel 28. A second side panel 30 is connected to each first side panel 26 by hinges 32 or the like, whereas a roof panel 34 is connected to the top panel 28 by further hinges 32. As is shown in FIG. 2, when not in use the roof panel 34 can be folded on top of the top panel 28, whereas the second side panels 30 can be folded against the back of the front part 24. The roof panel 34 may be foldable in two parts across a folding line 33 for compactness. As shown in FIG. 2, the operation unit 1 is in its folded position relatively small and can for example be manoeuvred through a door opening into and out of various rooms. To this end the operation unit 1 is preferably mounted on wheels 36.

As can be seen in for example FIG. 1, the front wall 2 is provided with a transparent part 38 above said opening 16, for example a window. As is shown in for example FIG. 4 and 7 a person 14 within said space 10 can have visual contact through said panel 38 with a person 14A positioned outside said space 10, for example a nurse an anaesthetist, the patient 15 or other people. The person 14 can also have visual contact with apparatuses in the area around said operation unit 1. The second side panels 30 are preferably made also of transparent material, such as glass or plastic.

In order to facilitate foldability of the operation unit 1, as shown in FIG. 2, the back wall 8 is preferably foldable and can for example be provided with a door 17 allowing entrance into said space 10. In a preferred embodiment however said back wall 8 is made of for example plastic strips extending from the roof 34, overlapping each other partly, such that said wall 8 can easily be traversed by a person, whereas the back wall 8 provides for a closed back wall during use. The back wall may have an opening over its full height of 10-50 cm in width, to allow the air to leave the operation unit 1 without causing turbulence.

Within the space 10 within said operation unit 1 an airflow unit 40 is provided comprising a duct 42 extending along parts of the two opposite sidewalls 4, behind the side panels 26 and across the front wall, below said top panel 28. The duct 42 is at one end 43 provided with an inlet opening 44 for air from within said space 10, whereas at an opposite end 45 the duct 42 is connected to an air outlet unit 46 extending across the width of the air unit 1 between the two legs 47 of the substantially U-shaped duct 42, under said transparent part 38 and across the opening 16. The length L of said air outlet unit 46 is larger than the width W of said opening 16 and corresponds preferably substantially to the width $W_1$ of said cover 22, of which in FIG. 3 only the right side is shown. Left to the centre line C said cover 22 is only shown by its contour 22, showing the opening the opening 16.

The air outlet unit 46 comprises an air outlet opening 48 extending over approximately the full length L of said air outlet unit 46. The air outlet opening 48 may also be provided as a series of smaller openings one beside the other. The air outlet opening 48 is preferably configured such that during use an airflow is provided for leaving said air outlet opening 48 in a direction downward, away from said front wall 2, as is shown schematically by the arrows F in the FIGS. 3-7.

In FIG. 6 the airflow within said unit is schematically shown, during use. This can be understood as follows.

Within the airflow unit 40, especially within said duct 42, pumping means 50 are positioned for generating an airflow. Furthermore, filtering means 60 are positioned within said duct 42 for filtering the air. The filtering means 60 are designed such that air flowing through said duct in the direction of the arrows $F_1$ is filtered such that sterile air leaves the air outlet opening 48 in the direction F during use. Sterile air has to be understood in this description as at least encompassing air sufficiently clean to be allowed in operation environments as discussed. To this end the pre filtering means can for example comprise a G3 or G4 filter, according to EN779 in combination with a pre filter means of type F7 to F9, according to EN779, upstream from said pumping means for filtering particles from the air, whereas a filtering means of the type $H_{14}$ according to EN1822 can be provided downstream from said pumping means 50 for further sterilisation of said air $F_1$.

During use air is sucked in through said at least one inlet opening 44 through said (pre) filtering means from said space 10 into the duct 42 by the pumping means 50, through said filtering means 60 into the direction of the air outlet unit 46. The air is then forced in the direction F downward and preferably away from the front wall over the cover 22 into the direction of the ground 20 and back into the direction of the inlet opening 44. This leads to recirculation of the air through the airflow unit 40, constantly sterilizing the air. As is clear from the drawings, the lower edge 18 of the walls 2 and/or 4 and/or 8 can be positioned during use a little above the ground 20, leaving an opening 19 just above the ground 20. This substantially prevents undesired pressure differences between the inner space 10 of the unit 1 and the surrounding 62. Therefore turbulence of air is substantially prevented.

Operation equipment such as a microscope 64 can be provided for within said space 10, for example on the air outlet unit 46 or on shelves (not shown) on either one of the walls 2, 4, 8 or on the outside of the duct 42.

An operation unit 1 according to the present invention can be used for a method as follows.

The operation unit 1 is brought to an operation site which may for example be in a clean room, an operation theatre, a sick room, a recovery room or any other room allowing sufficient space for setting up such operation unit. In specific circumstances the operation unit 1 could even be used outside buildings, for example on a military field, or on a disaster site. The unit is then set up in the position as shown in FIG. 1. A patient 15 is prepared for operation, for example by suitable anaesthetics or the like and placed on for example an operation table, a stretcher or the like, suitably supporting him. Apparatuses 66 can be attached to the patient 15 in the area 62 surrounding said unit 1, which does not have to be sterile. The patient 15 and any person 14A in said surroundings 62 may wear plane clothes and does not have to perform specific washing operations or the like.

In FIG. 4 schematically an operation is shown on a head 15A of a patient 15, for example an eye operation. To this end the head end of the operation bed 68 is pushed into the direction P through the opening 16, under the cover 22, such that the cover 22 rests on said head 15A covering said head 15A of the patient 15 and hanging down to near the floor 20. As is schematically shown in FIG. 3, an operation opening 70 is made in the cover 22, such that the operation site, such as an eye is accessible for the surgeon 14 through the cover 22, as is common in commonly known operation techniques. The airflow unit 40 is brought into operation, such that the airflow F is directed downward over the cover 22, into the direction of the surgeon 14, who may for example be sitting within said space 10 on a chair 72, having his knees against the cover 22, under the head end of the operation table 68. Due to the airflow F over the cover 22 the operation site is kept sterile, thereby preventing infection. The air is recirculated through the airflow unit 40, as discussed before, maintaining sufficient sterility within said space 10. Due to the transparency of at least part of the walls 2, 4, the surgeon 14 can keep visual contact with other persons 14A and the patient 15.

In FIG. 5 an alternative embodiment of an operation unit 1 is shown, in which similar parts have similar reference signs. In this embodiment the opening 16 is made such that an operation bed 68 can be introduced sideways into said opening 16, under said cover 22, such that for example an operation site on a stomach of a patient 15 can be made available through an opening 70 in said cover 22.

FIG. 5A shows an alternative unit 1, comprising two units 1 according to FIG. 5 placed against each other with the front walls 2. This provides for two spaces 10, one on each side of the patient 15, allowing access from both sides. Alternatively, these spaces 10 can be provided in one unit 1 and/or the outlet units 46 can be provided with air from the same unit 40 for blowing air over the cover 22.

In FIG. 7 a still further embodiment of an operation unit 1 according to the present invention is shown, which unit is in this embodiment stationary. The front wall 2 is extending between a roof 6 and a floor 20, an opening 16 being providing in said wall 2, behind which a cover 22 is provided as discussed before. Schematically, attachment means 23 are shown for said cover 22, comprising hooks in said wall 2 on which the cover 22 can be suspended. It will be clear that any kind of attachment means can be used here. A window 38 is provided for allowing visual contact between the space 10 within said unit 1, at one side of said wall 2 and the surrounding 62 on the opposite side. An airflow unit 40 is provided, comprising a duct 42 housing the pumping means 50 and filtering means 60 (not shown in FIG. 7). An air outlet unit 46 is once again provided extending across the opening 16, having an air outlet opening 48 for directing air F downward over said cover 22. The air may be recirculated again by introducing the air through an air inlet opening 44, as discussed before. The surgeon 14 can once again perform operations on a patient 15, whereas other people 14A can stay in these surroundings 62.

In FIG. 8 a further embodiment of an operation unit 1 according to the present invention is shown, in which corresponding parts have corresponding reference numbers. The operation unit 1 is shown in a view corresponding to FIG. 6, showing the airflow within.

In this embodiment an airflow F is generated substantially symmetrically by providing an airflow unit 40 comprising two air ducts 42 near both sides of the space 10, connected to an air duct 42A along the top of the unit 1. Within said top duct 42A pumping means 50 are positioned, for example a blower having suction ports 51 on both sides. Both ducts 42 are at the lower ends provided with air inlet openings 44, substantially covered by a first filter 60A. Near the top of the ducts 42 an UV-lamp 70 may be provided for treatment of the airflow. In the top duct 42A on both sides of the blower 50 second filtering means 60B are provided for further filtering of the airflow F. As can be seen in especially FIG. 9 between the air outlet unit 46 and the top duct 42A, especially the outlet 52 of the blower 50, two panels 38A, 38B are provided, which extend over the full width between the ducts 42, thus providing for a connecting duct 53 between the blower 50 and the air outlet unit 46. Said panels 38A, B are preferably transparent, for visibility. In the air outlet unit 46 and/or near the blower 50, especially the outlet 52 baffles or such means may be provided for guiding the air flow F such that when leaving the air outlet unit 46 the air is well divided over the width of the outlet unit 46, preferably substantially in a laminar flow. In the air outlet unit 46 preferably a third filtering means 60C is provided for providing sterilized air.

As can be seen from especially FIG. 8, in an embodiment of an operation unit 1 according to FIGS. 8 and 9 a substantially symmetrical airflow is generated through said air unit 40, which is favourable for air distribution.

In operation units 1 according to the present invention it is preferred that the final filtering means, for example, filter means 60C are provided in or near the air outlet unit 46, sterilizing the air finally just before leaving the air outlet unit 46. In the embodiment in FIG. 8 secondary air inlet openings 71 are provided near the top of the operation unit 1, for example at the top of the air ducts 42. These openings are provided with an air regulating means such as a hinged lid 72, which can define the airflow through said secondary air inlet opening 71. Fourth filtering means 60D are provided near said secondary air inlet opening 71, for filtering the incoming air.

By way of example, which should not be interpreted in any way limiting the scope of the present invention, in a unit according to FIG. 8, the first filtering means can be a first step pre filter 60A, for example a G3 or G4 filter, according to EN779, the second filtering means could be a second step filter 60B, for example an F7 to F9 filter, according to EN779, whereas the third filtering means could be an end filter, for example a H14 Hepa filter, according to EN1822. The fourth filtering means could be a first step filter similar to the first filtering means 60A. In the air ducts 42 an air speed is preferably generated according to the specifications of the filtering means, for example between 1 and 2 m/second, especially around 1.5 m/second. The UV-lamp 70 is for example a low Watt lamp, for example around 8 Watt. The distance between the first filtering means 60A and the UV-lamp is for example 1 to 2 m, preferably around 1.5 m. Within the top duct 42A, especially near the blower 50 the air speed is preferably somewhat lower, for example around 0.5 m/second. It will be clear that for different configurations and for different purposes of use of a unit according to the present invention these may be varied.

For an operation unit according to the invention, especially in an embodiment as shown in FIG. 7, obviously the airflow unit 40 can also be connected to a source of sterile air as commonly known for, for example operation rooms.

Every combination of parts of the various embodiments shown in this description are considered to be described here and fall within the scope of the present invention.

The present invention is by no means limited to the embodiments as shown and described in the figures and description. Many similar embodiments may be contemplated.

For example, an operation unit according to the present invention may have non-foldable walls and a roof, whereas the airflow unit may be suspended within said unit, instead of forming part of the frame thereof, as is shown in the drawings or placed outside said unit. Moreover, a unit according to the present invention could be hanging from a ceiling or roof. The air flow unit 40 may have any suitable form and size for providing a suitable flow of sterile air over said cover 22 during operation which may have a different direction. The cover 22 is preferably made of cloth or the like, but may also be made of other material, for example more rigid. As is shown in FIG. 3, the unit may be provided with connecting means 80, for connecting to a supply of electrical current, for the flow unit, operation means and the like. However, the unit may also be provided with an aggregate for providing said electrical current, or other means for generating sufficient energy.

These and various other variants, including any combination of features of the embodiments shown and described are considered to fall within the scope of protection, defined by the attached claims.

The invention claimed is:

1. An operation unit, comprising an enclosed space formed from at least two side walls, a back wall, a front wall, and a top wall connected to the two side walls, the back wall and the front wall, the operation unit further including an air flow unit, said air flow unit having a duct and a pumping means and filtering means within the duct, said front wall being provided with at least one opening and a cover that hangs down from above the opening and having a width larger than the width of the opening and a height larger than the height of the opening with the cover having an operation opening corresponding to an operation site on a patient, said air flow unit comprising at least one air outlet unit having an air outlet opening extending over the length of the air outlet unit and within the enclosed space and the air outlet unit extending above and over the width of the opening and substantially directing air from said air flow unit downward and substantially in a laminar flow and away from the front wall and over said cover and the operation opening and toward an air inlet within the enclosed space and positioned below the operation opening for retracting air from within said enclosed space to said air flow unit.

2. An operation unit according to claim 1, which unit is at least partly foldable.

3. An operation unit according to claim 2, in which the side walls and top wall are foldable over and/or against said flow unit, the back wall preferably being foldable and/or made of strip-like elements.

4. An operation unit according to claim 1, in which said cover is a surgery blanket substantially made of cloth or plastic.

5. An operation unit according to claim 1, in which said at least one opening in the front wall is dimensioned such that at least an end of a hospital bed, stretcher or the like can be inserted through said opening under said cover.

6. An operation unit according to claim 1, in which said at least one opening in the front wall is dimensioned such that an extremity of a person can be inserted at least partly through said opening under said cover.

7. An operation unit according to claim 1, in which openings are provided near the ground for connection of an inner space of said unit and the surrounding.

8. An operation unit according to claim 1, in which at least part of one or more of said front wall, side walls and a back wall of said unit are made transparent.

9. An operation unit according to claim 1, in which said unit is provided with wheels for easy displacement of said unit.

10. An operation unit according to claim 1, in which the air flow unit is provided near the upper end of said front wall and is connected to the air outlet unit by a first connecting pipe and to the air inlet by a second connecting pipe, said connecting pipes being provided near either side of said front wall to form part of a frame of said operation unit.

11. A method for preparing a person for surgery, in which said person is positioned on a bed, stretcher, chair or the like supporting structure, whereby part of the body of said person on which surgery is to be performed is moved into an operation unit comprising an enclosed space formed from at least two side walls, a back wall, a front wall, and a top wall connected to the two side walls, the back wall and the front wall, the operation unit further including an air flow unit, said air flow unit having a duct and a pumping means and filtering means within the duct, said front wall being provided with at least one opening and a cover that hangs down from above the opening and having a width larger than the width of the opening and a height larger than the height of the opening with the cover having an operation opening corresponding to an operation site on a patient, said air flow unit comprising at least one air outlet unit having an air outlet opening extending over the length of the air outlet unit and within the enclosed space and the air outlet unit extending above and over the width of the opening and substantially directing air from said air flow unit downward and substantially in a laminar flow and away from the front wall and over said cover and the operation opening and toward an air inlet within the enclosed space and positioned below the operation opening for retracting air from within said enclosed space to said air flow unit.

12. A method according to claim 11, in which said air is recirculated through a flow unit filtering said air for sterilisation purposes.

13. A method for performing surgery on a person, in which said person is positioned on a bed, stretcher, chair or the like supporting structure, whereby part of the body of said person on which surgery is to be performed is moved into an operation unit comprising an enclosed space formed from at least two side walls, a back wall, a front wall, and a top wall connected to the two side walls, the back wall and the front wall, the operation unit further including an air flow unit, said air flow unit having a duct and a pumping means and filtering means within the duct, said front wall being provided with at least one opening and a cover that hangs down from above the opening and having a width larger than the width of the opening and a height larger than the height of the opening with the cover having an operation opening corresponding to an operation site on a patient, said air flow unit comprising at least one air outlet unit having an air outlet opening extending over the length of the air outlet unit and within the enclosed space and the air outlet unit extending above and over the width of the opening and substantially directing air from said air flow unit downward and substantially in a laminar flow and away from the front wall and over said cover and the operation opening and toward an air inlet within the enclosed space and positioned below the operation opening for retracting air from within said enclosed space to said air flow unit; and performing surgery on the person.

14. An operation unit according to claim 1, wherein the front wall includes a transparent part provided above said opening, said at least one air outlet opening being provided between said transparent part and said opening.

15. An operation unit according to claim 1, wherein the air outlet opening includes one or more outlet openings.

16. An operation unit according to claim 1, wherein the duct extends along the two sidewalls and across the front wall and below a transparent part of said front wall above said opening.

17. An operation unit according to claim 1, wherein between a lower edge of at least one wall and a floor on which said unit is placed at least one gap is provided, lower than the air inlet, for pressure equalisation between the enclosed space of the unit and the environment thereof.

* * * * *